United States Patent [19]
Neill et al.

[11] Patent Number: 5,907,086
[45] Date of Patent: May 25, 1999

[54] PLANT PROMOTER SEQUENCES

[75] Inventors: John Neill, Des Moines; John Howard, West Des Moines, both of Iowa

[73] Assignee: Pioneer Hi-Bred International, Inc., Des Moines, Iowa

[21] Appl. No.: 07/694,227

[22] Filed: May 1, 1991

[51] Int. Cl.$^6$ .............. A01H 5/00; C12N 15/82; C12N 5/04
[52] U.S. Cl. ............ 800/295; 435/69.1; 435/468; 435/419; 435/320.1; 536/24.1
[58] Field of Search .............. 800/205; 536/27, 536/24.1; 435/172.1, 172.3, 240.4, 240.49, 320.1, 419; 935/6, 30, 35, 67

[56] References Cited

U.S. PATENT DOCUMENTS 4,885,357  12/1989  Larkins et al. .................... 530/373

FOREIGN PATENT DOCUMENTS

| | | |
|---|---|---|
| 89103888 | 3/1989 | European Pat. Off. |
| 90302740 | 3/1990 | European Pat. Off. |
| 91305310 | 6/1992 | European Pat. Off. |
| 89/02151 | 5/1989 | U.S. ................ G01N 33/48 |
| 90/00101 | 1/1990 | WIPO |
| 90/00110 | 1/1990 | WIPO |

OTHER PUBLICATIONS

Shah, D.M., et al., Plant Mol. Biol., 6:203–211 (1986), Dordrecht, NL, "Structural analysis of a maize gene coding for glutathione–S–transferase involved in herbicide detoxifications".

Wiegand, R.C., et al., Plant Mol. Biol., 7:235–243 (1986), Dordrecht, NL, "Messenger RNA encoding a glutathione–S–transferase responsible for herbicide tolerance in maize is induced in response to safener treatment".

Grove, G., et al., Nucleic Acids Research, vol. 16, (2), pp. 425–438 (1988), London, GB, "Characterization and heterospecific expression of cDNA clones of genes in the maize GSH–S–transferase multigene family".

Deikman et al., (1988) EMBO J. 7 (11):3315–3320.

*Primary Examiner*—Elizabeth F. McElwain
*Attorney, Agent, or Firm*—Patricia A. Sweeney

[57] ABSTRACT

A chemically inducible, heat-shock inducible and general-purpose plant gene promoter sequence, and expression cassettes, plant cells and plants containing the sequence.

12 Claims, 14 Drawing Sheets

PLANT PROMOTER SEQUENCES

TECHNICAL FIELD

The present invention relates to promoters for the expression and control of gene activity in plants.

BACKGROUND ART

In many instances in the genetic engineering of plants in which a gene is inserted into the genome of a plant, it is desirable to be able to control expression of the gene. In other instances, it is desirable to be able to modify the expression of a gene which is native to the genome.

For example, in the creation of male sterility for the purpose of hybridizing crops, it is possible to select a gene which is normally required for pollen formation and inactivate that gene by insert a normally inactive promoter into the control sequences for the gene, so that the gene is "turned off" and the plant becomes male sterile, i.e., incapable of producing pollen. This system is disclosed in the copending application of Albertsen et al., Ser. No. 07/537,183, Filed Jun. 12, 1990. In order to reproduce plants of the modified genotype, it would be necessary to activate the promoter, desirably by some exogenous stimulus. Accordingly, a continuing need exists for promoters which are responsive to external stimuli such as non-phytotoxic chemicals.

In other instances it is desirable to place the expression of a gene under the control of a promoter which is responsive to unusual environmental conditions, such as drought and heat shock.

DISCLOSURE OF THE INVENTION

The present invention provides a promoter system from the glutathione-S-transferase I (GST I) system in maize. GSTs are a family of enzymes that can detoxify a number of hydrophobic electrophilic compounds that often are used as pre-emergence herbicides (Wiegand, et al., "Messenger RNA Encoding a Glutathione-S-Transferase Responsible for Herbicide Tolerance in Maize is Induced in Response to Safener Treatment". Plant Molecular Biology 7: 235–243, 1986). It has been discovered that treating maize seed with GSTs increases the tolerance of the maize to the herbicides. Studies have shown that the GSTs are directly involved in causing this enhanced tolerance. This action is primarily mediated through a specific 0.9 kb mRNA transcription product. In short, maize has a series of naturally occurring genes already present that can respond to exogenous chemicals and that can be induced to produce a gene product. One such gene has already been identified and cloned.

It has also been determined that the promoter system provided herein is responsive to heat shock. Thus, a gene which is beneficial to the plant under conditions of heat shock can be inserted into the genome of the plant under the control of this promoter sequence and the inserted gene will be expressed when the plant is subjected to heat shock.

Accordingly, the present invention provides a plant gene promoter having the sequence listed in SEQ. ID. NO. 1. This promoter can be readily inserted using known methods into an expression cassette for the expression in plants of a selected gene. Preferably, the promoter is operatively linked upstream from a gene which codes for a protein expressible in a plant other than glutathione-S-transferase. Such proteins desirably include seed storage proteins, enzymes other than glutathione-S-transferase, transcriptional activators, and insecticidal lectins. This cassette can be inserted using known techniques, including electroporation, microparticle bombardment, microinjection, and Agrobacterium tumefaciens infection, into plant cells of a target species. Thus, this invention also provides plant cells, the genome of which comprises an expression cassette containing the promoter of this invention. Whole plants comprising such cells will have the features or benefits provided by expression of the protein. Such plants can be dicots or monocots, including, without limitation, species from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Triticum, and Datura.

Preferred plants that are to be transformed according to the methods of this invention are cereal crops, including maize, rye, barley, wheat, sorghum, oats, millet, rice, triticale, sunflower, alfalfa, rape seed and soybean.

INDUSTRIAL APPLICABILITY

The following examples illustrate the practice of this invention without intending to be limitative thereof.

EXAMPLE I

Isolation of the GST1 Promoter Region

A GSTI cDNA clone was obtained from a dichlormid-induced root cDNA lambda library by probing with a synthetic oligonucleotide probe. The sequence of the probe was obtained from Moore et al., "Cloning and Expression of A cDNA Encoding a Maize Glutathione -S-Transferase in *E. Coli.*", *Nuc. Acids Res.* 14:7227–7235. 1983. Positive plaques were purified and restriction mapped to confirm identity. One GSTI cDNA was used to probe a W22 genomic lambda library. A positive plaque was grown and restriction mapped to confirm identity. This clone contained the 5' end of the GSTI gene as well as all of the promoter region. The promoter region was subcloned in pGEM4Z and was sequenced and the sequence identified as indicated in SEQ. ID. NO.1.

EXAMPLE II

Cell Culture

Maize embryonic suspension cells, genotype 3-44-6, were maintained in medium 237 (MS salts and vitamins, 100 mg/l myo-inositol, 2 mg/l 2,4-D, 0.05 mg/l zeatin, and 3% sucrose). The pretreatment medium consisted of medium 237 containing 250 mM mannitol.

On day 0, cells were sieved through a 710 $\mu$m screen to reduce and equalize cell group sizes. All liquid was removed and the cells were weighed. One gram of cells was placed in non-baffled flasks and resuspended in 20 ml of medium 237 (control treatment) or 20 ml of medium 237 containing 0.01% Teepol and 15 ul.l dichlormid (induction treatment). Suspensions of both were shaken at 100 rpm at 28° C.

On day 3, spent medium was removed from both cultures. The medium on the control cells was replaced with 20 ml of medium 237 containing 250 mm mannitol and the medium on the induced cells was replaced with 20 ml medium 237 containing 250 mM mannitol, 0.01% Teepol and 15 ul/l dichlormid. The suspensions were shaken at 100 rpm at 28° C.

On day 4, cells from both treatments were plated onto 2 grade 617 filter papers which were pre-moistened with medium 237 and 1 ml of 250 mM mannitol. One-half ml of cells were plated to yield 25 g of cells per plate. Cells were centered on each plate to maximize exposure to bombardment.

EXAMPLE III

Maize Embryo Preparation

Seeds of the maize public inbred line B73 were surface sterilized in 20% hypochlorite solution containing 0.5% Tween 20 for 20 minutes at room temperature. The seeds were rinsed thoroughly in sterile deionized water and imbibed in sterile petri plates with water containing 0.01% Teepol (control) or 0.01% Teepol and 15 ul/l of dichlormid (induced). The plates were placed in the dark at 28° C. for 3 days. The coleoptile tip was dissected from each seed and was placed on medium 272 (MS salts, 4% sucrose) overnight. The coleoptile tips (2) were centered on each plate to maximize exposure to bombardment.

EXAMPLE IV

Microprojectile Bombardment

Cells were bombarded using the DuPont helium-powered particle delivery system using 10 $\mu$g DNA concentration, precipitated onto tungsten with $CaCl_2$ and spermidine. All cells were bombarded one time using the following system settings:

Variable nest: high
Fixed nest: high
650 psi rupture disk

Following bombardment, cells on filters were transferred to medium 115 (AT base, 1 g/l myo-inositol, 0.75 mg/l 2,4-D, 700 mg/l proline and 2% sucrose) and incubated in the dark at 28° C. overnight. Coleoptile tips remained on the 272 medium and were incubated in the same manner. Enzymatic assays were done at 24 hours post-bombardment.

EXAMPLE V

Plasmids

Plasmids were derived from the following plasmids which contained the GST promoter: pGST92 (pPHI1511), pGST93 (pPHI1512), pGST94 (pPHI1513), and pGST95 (pPHI1514). Plasmids pGST46 (pPHI1361), pGST96 (pPHI1515), pGST97 (pPHI1516), pGST98 (pPHI1517), and pGST99 (pPHI1518). Plasmids containing luciferase were designated pGST100 (pPHI1519), pGST101 (pPHI1520), pGST102 (pPHI1521), pGST103 (pPHI1522), and pGST104 (pPHI1655) were obtained, as shown in the Figures.

EXAMPLE VI

Luciferase and GUS Assays

GUS enzymatic activity was detected by cytochemical staining of the bombarded tissues. One day following bombardment, the tissue to be assayed was transferred to a new plate and overlayed with GUS cytochemical substrate (100 mM potassium phosphate, pH 7.5), 5 mM potassium ferricyanide ($3^+$ Fe), 5 mM potassium ferrocyanide ($2^+$ Fe), 2 mM X-gluc., 5 1% DMSO). Suspension cells were overlayed with 400 $\mu$l of GUS substrate. Coleoptile tips were placed in a well of a microtiter plate, and 100 $\mu$l of GUS substrate was added. Tissues were incubated at 37° C. for 4 to 6 hours. Blue spots were counted under a dissecting microscope.

Luciferase enzymatic activity was determined after grinding bombarded samples in 200 $\mu$l of luciferase grinding buffer (100 mM potassium phosphate (pH 7.8), 1 mM DTT). The cellular debris was pelleted by centrifugation in a microcentrifuge at 4° C. Luciferase activity was assayed by addition of 200 $\mu$l of luciferase assay buffer (25 mM Tricine (pH 7.8), 15 mM $MgCl_2$, 5 mM ATP, 500 $\mu$g/ml BSA) and 10–20 $\mu$l of tissue extract into a 12×31 mm glass luminometer cuvette. The cuvette was placed into the luminometer and the reaction was initiated by addition of 100 $\mu$l of 500 $\mu$m luciferin (potassium salt) to the cuvette. The reaction was read as light units obtained from the LED readout.

The GST promoter functioned to drive expression of both GUS and luciferase reporter genes to levels of 10% to 50% of the CaMV 35S promoter. These levels of activity were very reproducible. We were also able to obtain induction in the number of GUS staining cells over that obtained from the untreated control cells using plasmid pGST46 (DP1361). The ratio of staining cells in treated versus untreated controls was 2.2 after 48 hours incubation with safener, 5.3 after 72 hours, and 4.4 after 94 hours of incubation in safener. Control experiments using CaMV 35S fused to GUS showed no induction whatsoever. Induction was not observed in the fluorescent GUS assay or when using luciferase as the reporter gene.

EXAMPLE VII

Nuclear Extracts

Extracts were prepared from dichlormid treated and non-treated corn roots. Seeds were planted in flats filled with perlite (100 seeds per flat) and were imbibed with water or water containing 15 ul/l dichlormid and 0.01 Teepol. The seeds were germinated and grown under greenhouse conditions. When the seedlings were approximately 1.5 inches tall, the flats were transferred to environmental chambers and were maintained in total darkness for two days. The temperature was 85° F. for 16 hours and 72° F. for 8 hours. The roots were collected, flash frozen in liquid nitrogen, and ground to a fine powder in a Waring blender. The frozen powder was placed in 200 ml of buffer A (10 mM MES (pH 6.0), 10 mM NaCl, 5 mM EDTA, 0.15 mM spermine, 0.5 mM spermidine, 20 mM 2-ME, 0.2 mM PMSF, 0.6% Triton X-100, 250 mM sucrose). The homogenate was stirred thoroughly and was filtered twice through 2 sheets of miracloth. The filtrate was centrifuged at 2000 G in a Sorvall GSA rotor at 4° C. and the pellet was resuspended gently in 20 ml of buffer A. The nuclei were pelleted again by centrifugation at 2000 G in a Sorvall SS-34 rotor. The pellet was gently resuspended in 2 ml of high salt buffer (20 mM HEPES (pH 7.9), 25% glycerol, 420 mM NaCl, 1.5 mM $MgCl_2$, 0.2 mM EDTA, 0.5 mM PMSF, 0.5 mM DTT). The nuclei were lysed by the addition of 4 M $(NH_4)_2SO_4$ to a final concentration of 0.3 mM. This was placed on ice with occasional mixing for 30 minutes. The starch and debris are removed by centrifugation in an Eppendorf microcentrifuge for 10 minutes at 4° C. The supernatant was transferred to a small beaker (on ice) containing a small stirring bar. Granular $(NH_4)_2SO_4$ (0.25 g/ml nuclear lysate) was added slowly until it was in solution. The solution was allowed to stir for an additional 30 minutes on ice. The insoluble proteins were pelleted by centrifugation for 10 minutes at 4° C. The pellet was resuspended in 0.5 ml of high salt buffer, and the protein solution was placed in a prepared dialysis membrane and dialysed against at least 4 changes of 500 volumes of cold dialysis buffer (20 mM HEPES (pH 7.6), 20% glycerol, 100 mM KCl, 0.2 mM EDTA, 0.5 mM DTT, 0.5 mM PMSF). Total dialysis time was 6 to 8 hours. The extract was aliquoted (50 ul) into microcentrifuge tubes, flash frozen in liquid nitrogen and stored at −80° C. until use. Protein concentrations were determined by the Bradford procedure.

EXAMPLE VIII

Gel Shift Analysis

The nuclear extracts were used in gel shift analysis to locate potential cis-acting regulatory elements within the GSTI promoter sequences. Specific restriction fragments from the GSTI promoter were end-labeled with $^{32}$P-dXTP (a labeling mix with all four radiolabeled deoxy-nucleotides) and purified from the unincorporated nucleotides by spun column chromatography. The amount of incorporation was measured in a scintillation counter. Approximately 20,000 cpm was used per binding reaction. The binding reaction consisted of 10 mM Tris-HCl (pH 7.6), 1 mM EDTA, 1 mM DTT, 1 μg of poly dI:dC (non-specific competitor), volume of extract to provide 2 μg of nuclear protein, 4 mM MgCl$_2$ (optional depending upon the divalent cation requirements of the specific DNA-binding protein) in a total volume of 25 ul. In specific competition experiments, 1 μg of unlabeled specific fragment was included in the binding reaction. The binding reactions were incubated at room temperature for 15 minutes and were loaded on a 6% polyacrylamide gel utilizing a Tris-glycine buffer system (25 mM Tris-HCl (pH 8.3), 190 mM glycine, 1 mM EDTA). The gel (which was pre-run for two hours) was run until the bromophenol blue in the loading dye migrated to an inch above the bottom of the gel. The gel was removed from the apparatus, dried and was used to expose X-ray film overnight on intensifying screens at −80° C. The band pattern on the film was analyzed for shift in band patterns due to binding of nuclear proteins to putative, cis-acting regulatory sequences.

Figure 1:
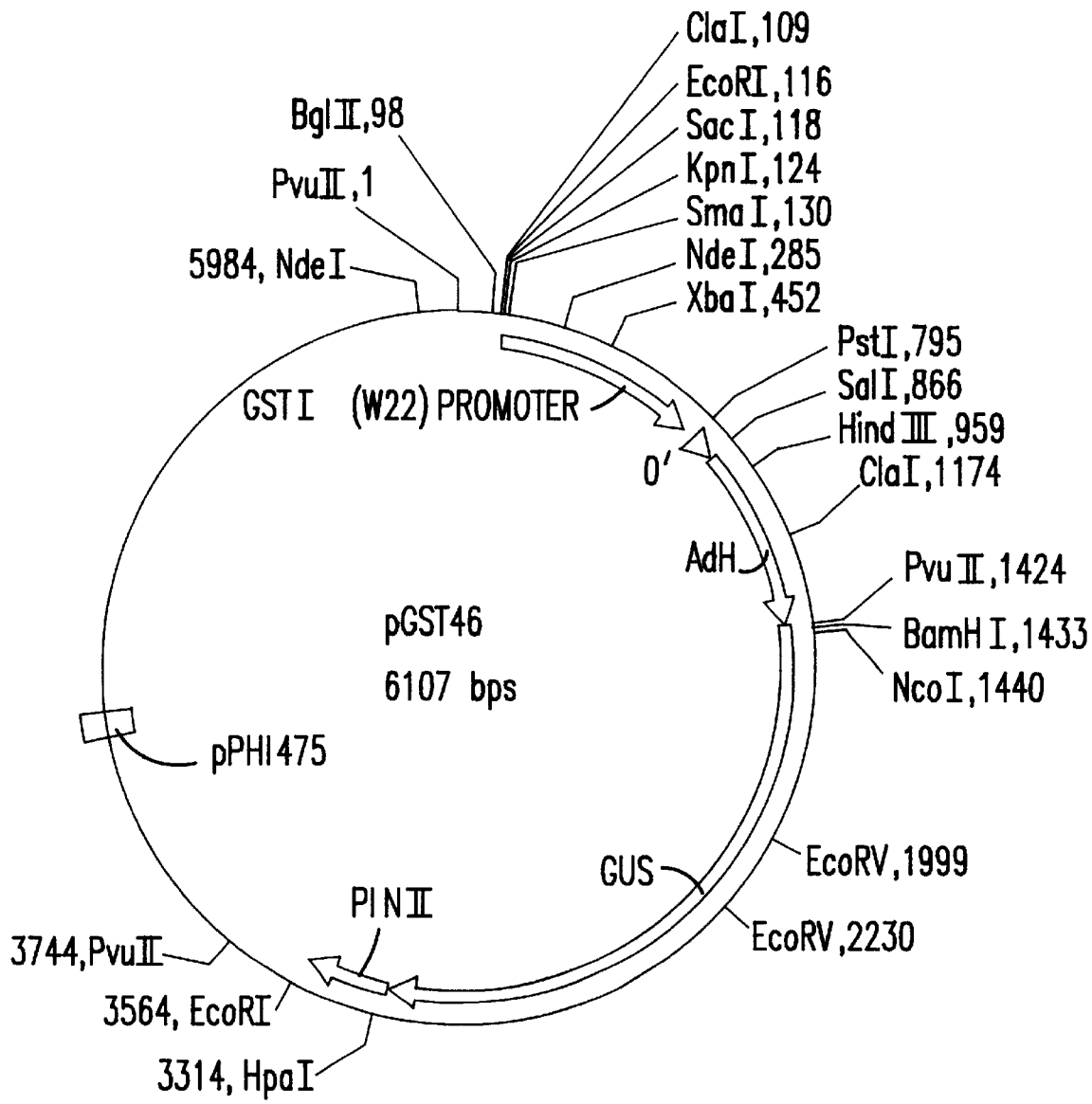
FIGS. 1–14 are plasmid maps of pGST46, pGST104, pGST103, pGST102, pGST101, pGST100, pGST99, pGST98, pGST97, pGST96, pGST95, pGST94, pGST93, and pGST92, respectively.
Figure 2:
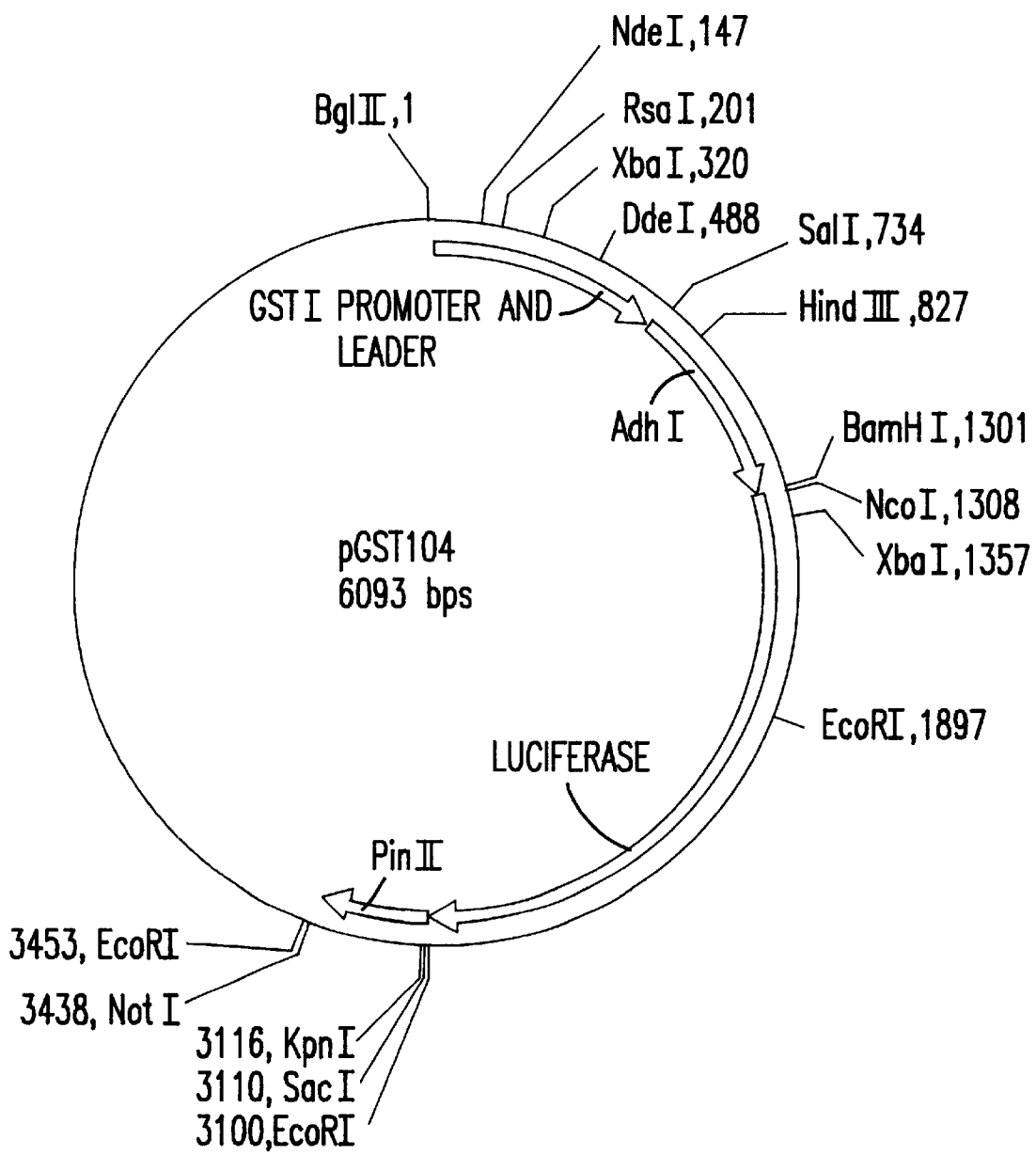
Figure 3:
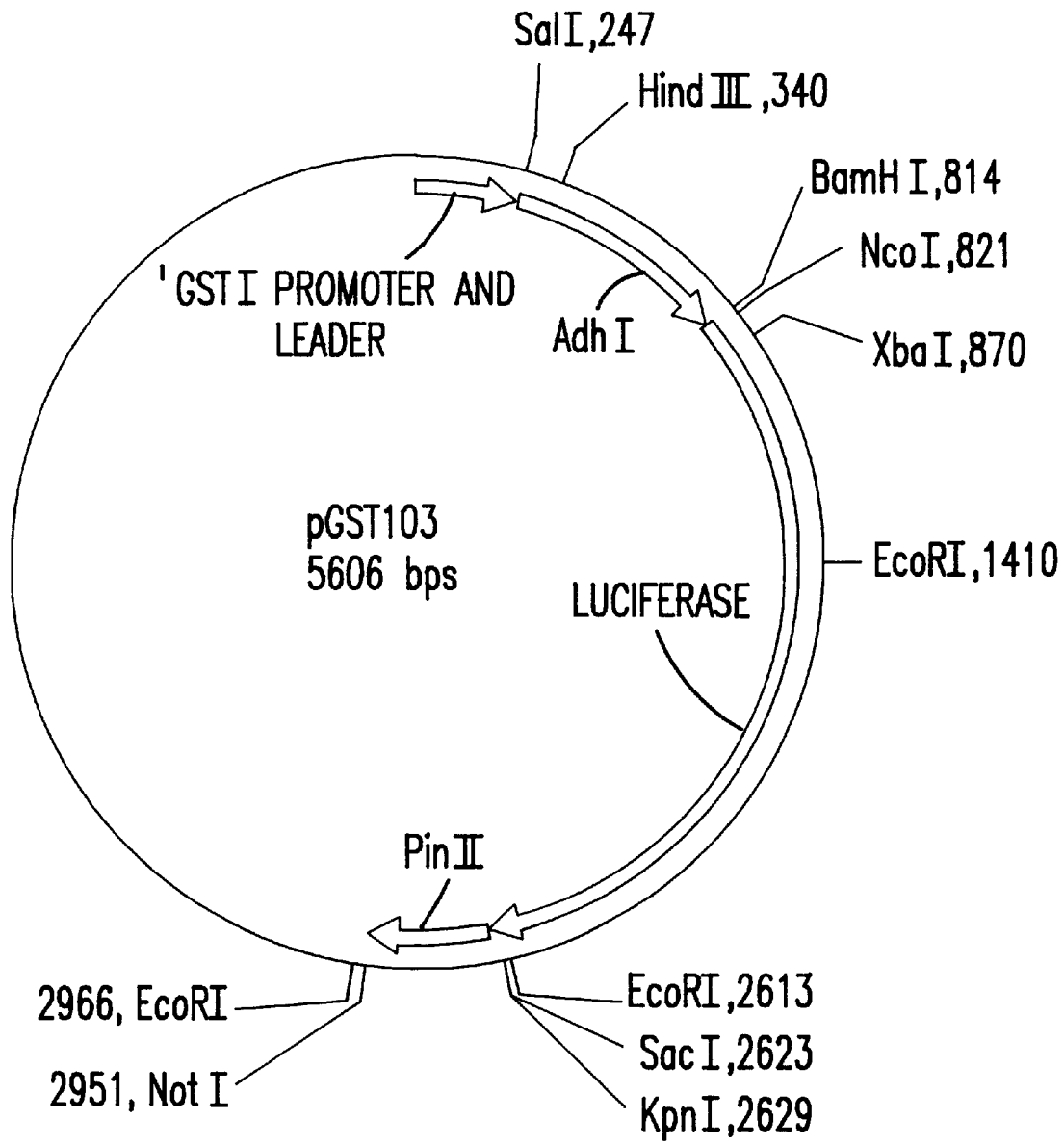
Figure 4:
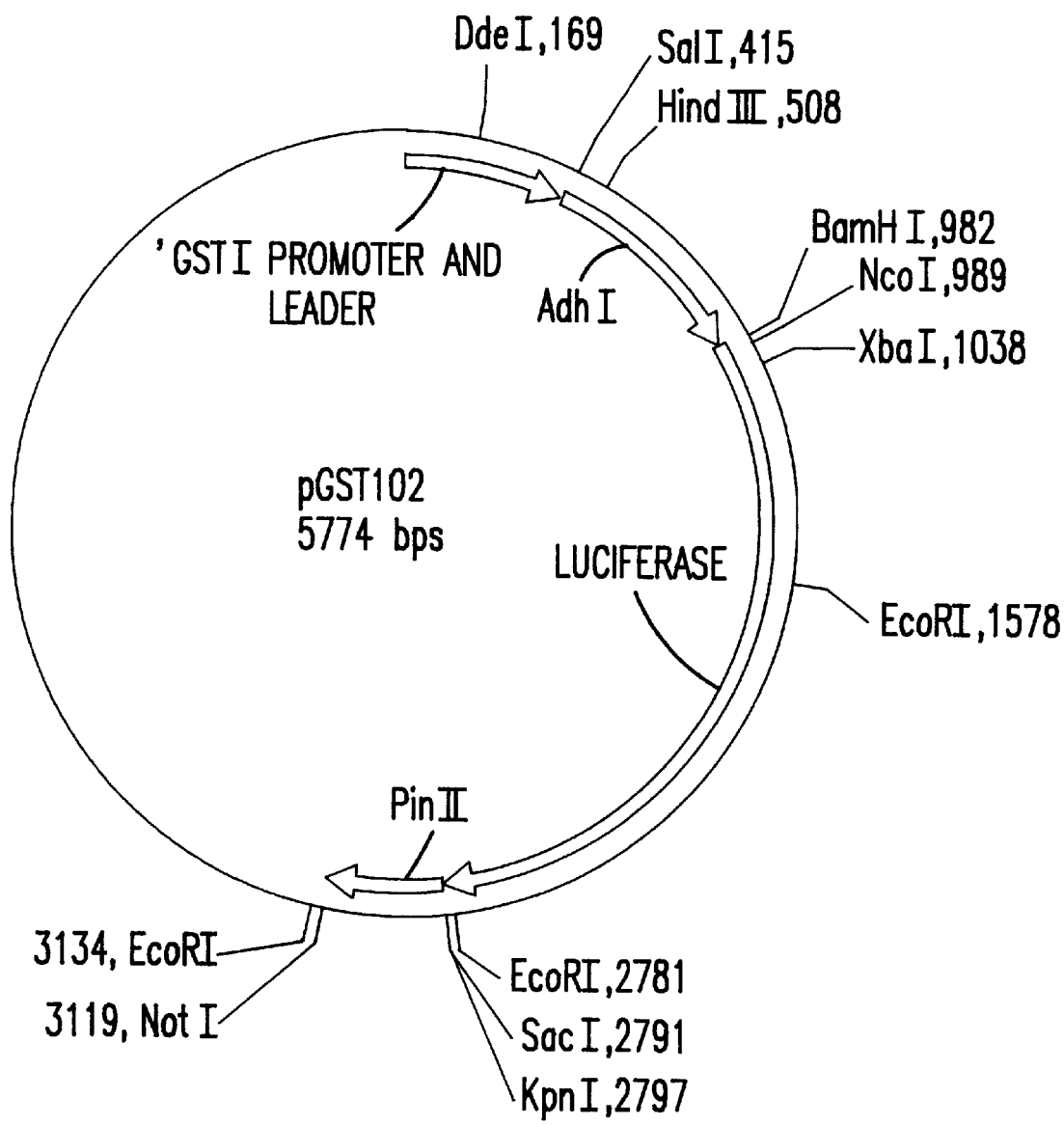
Figure 5:
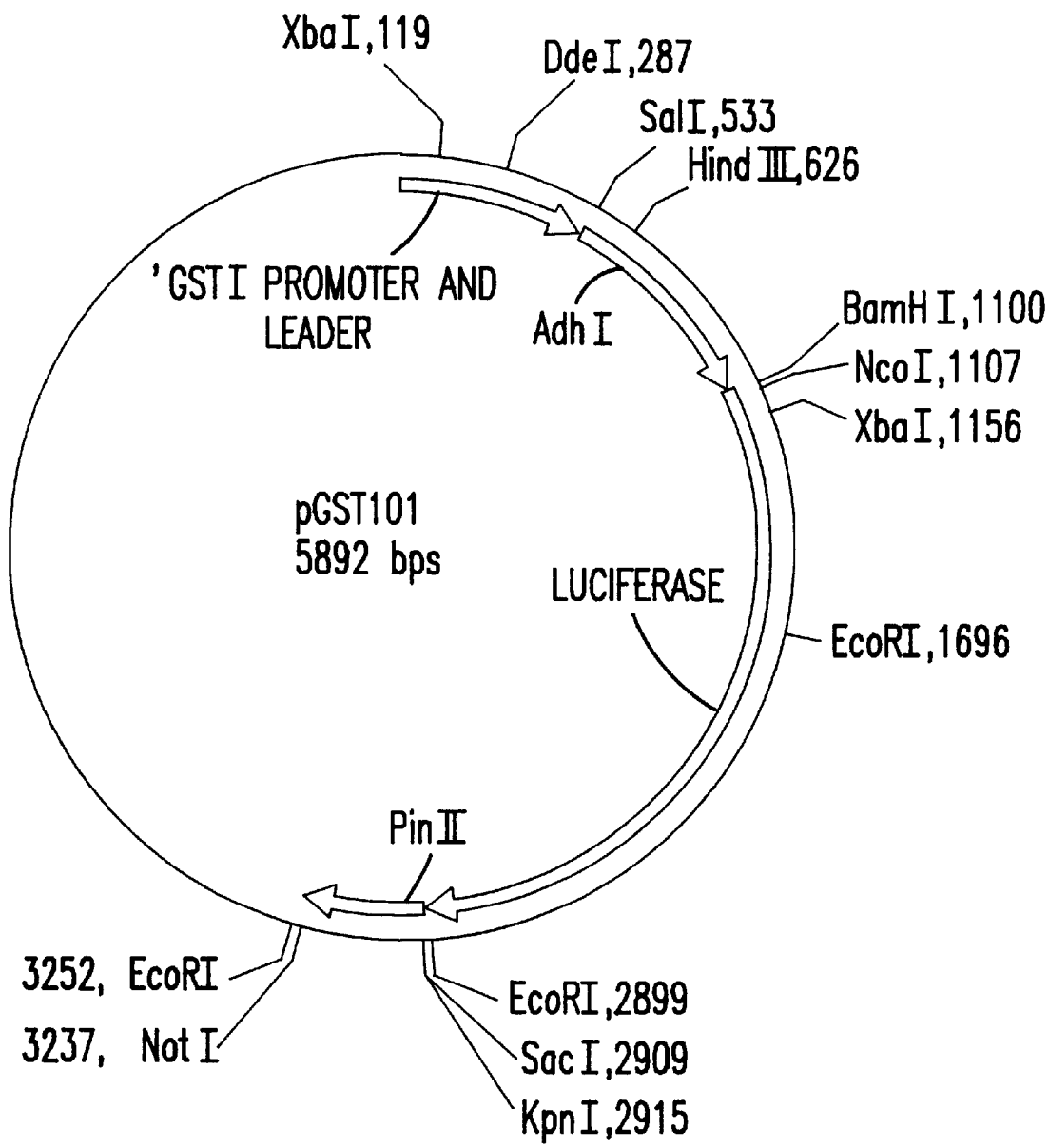
Figure 6:
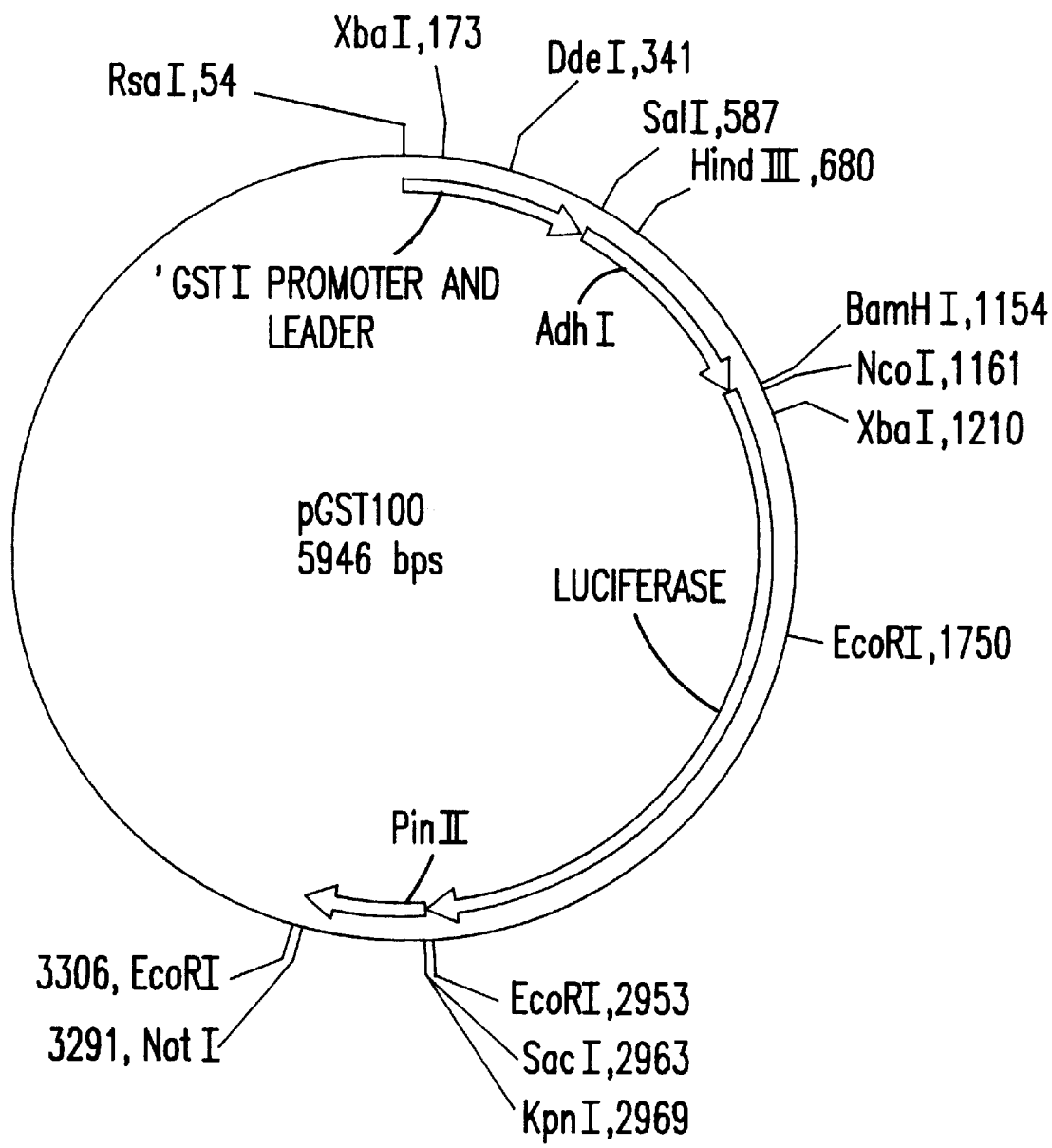
Figure 7:
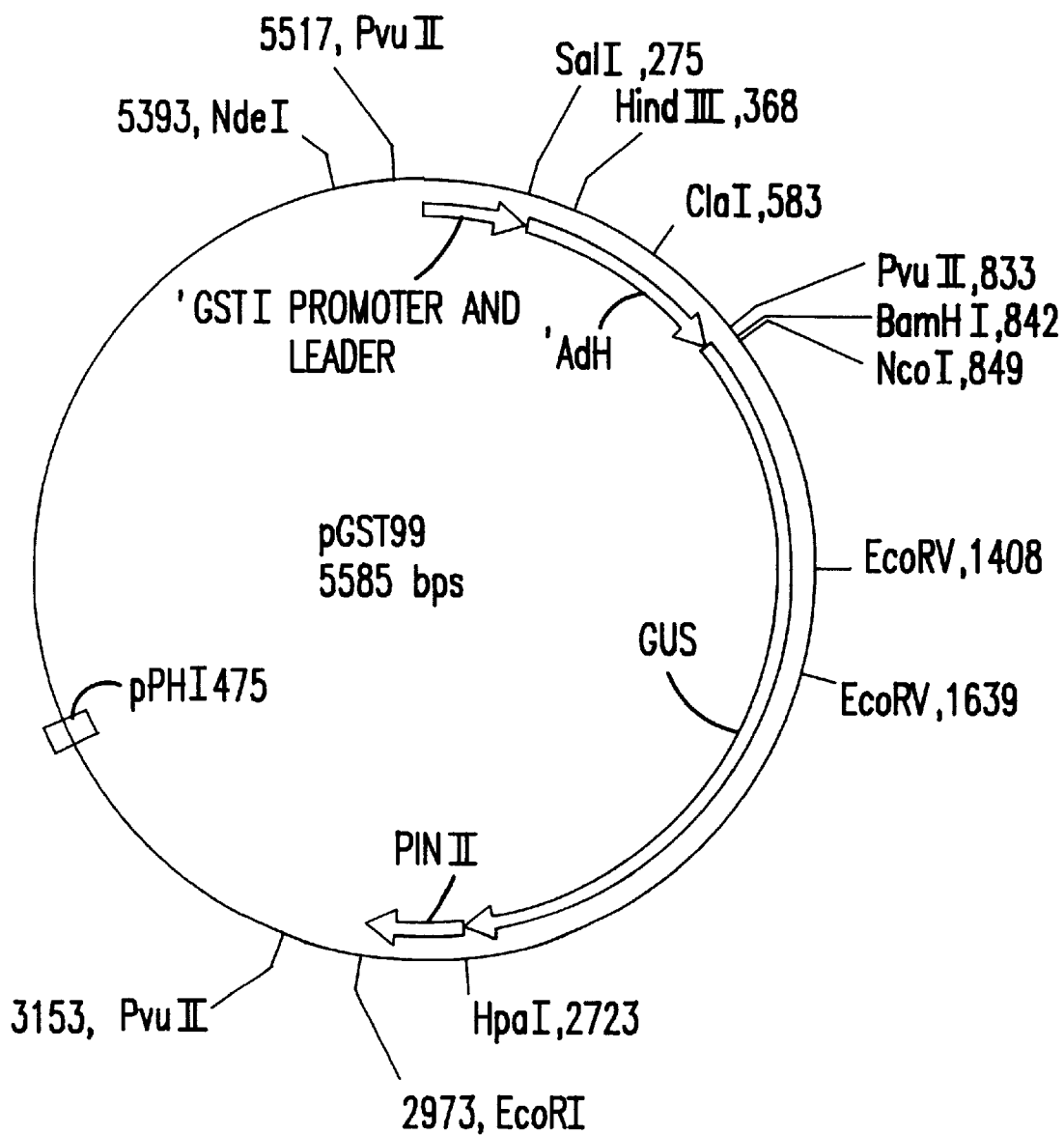
Figure 8:
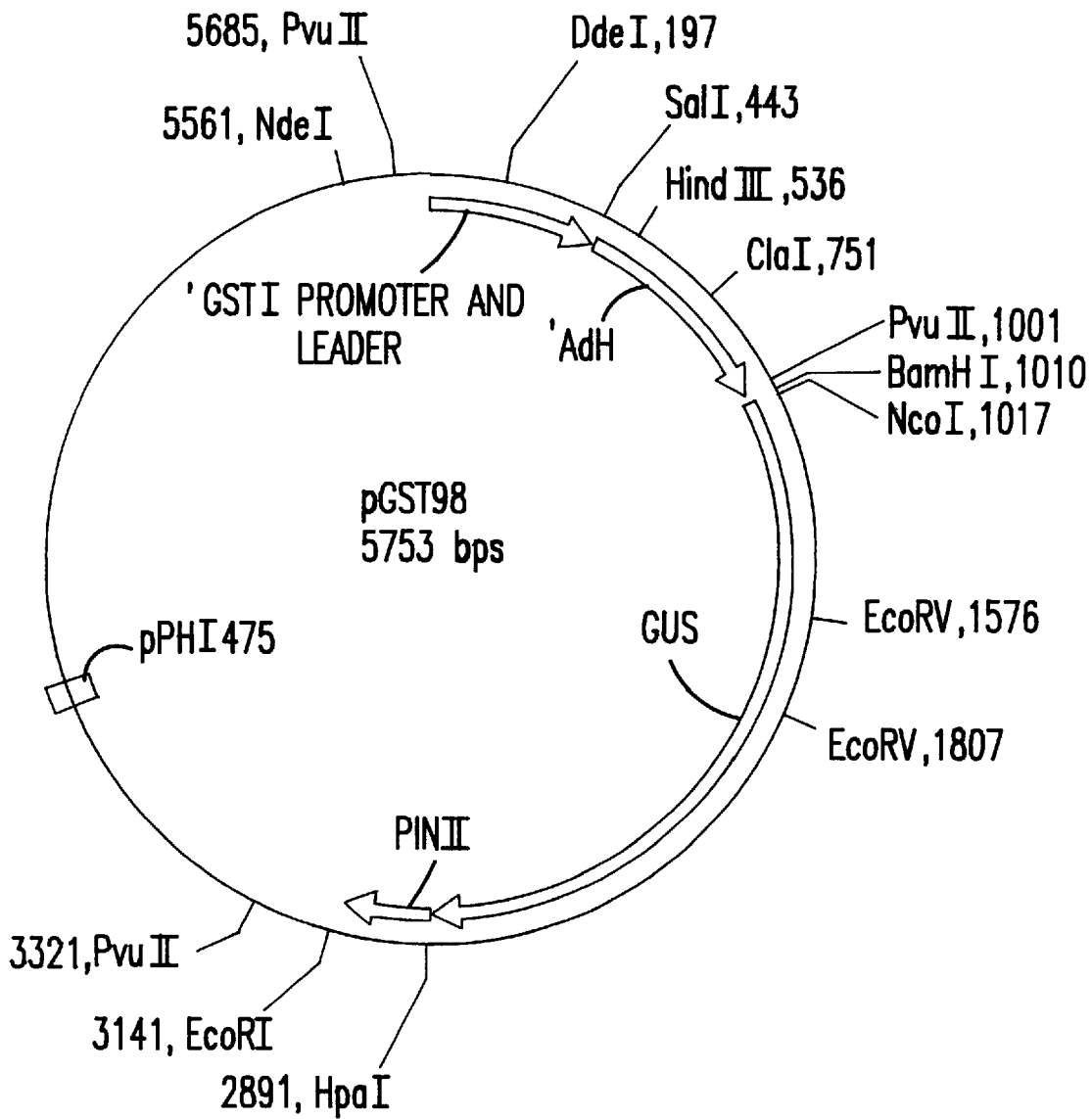
Figure 9:
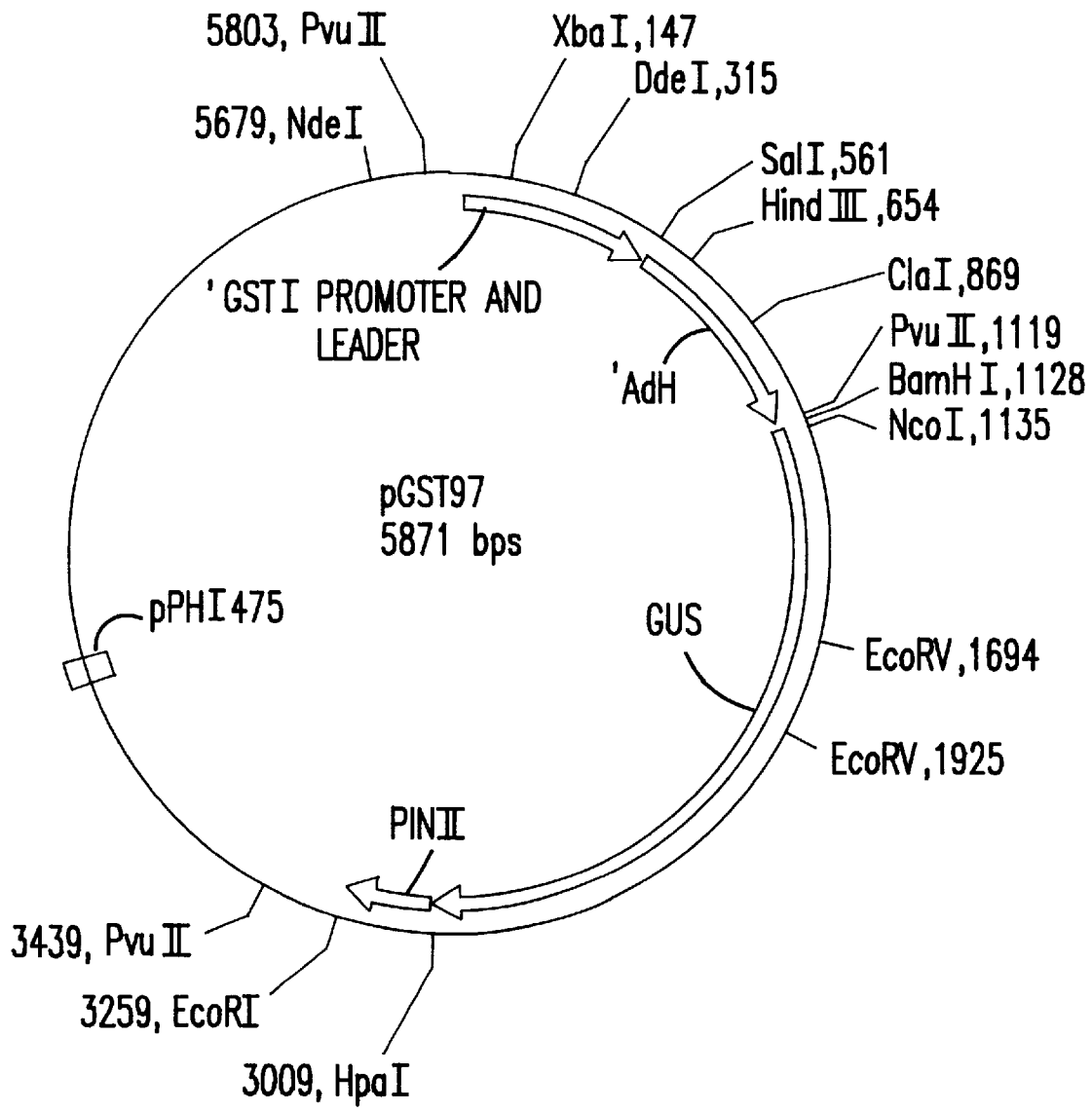
Figure 10:
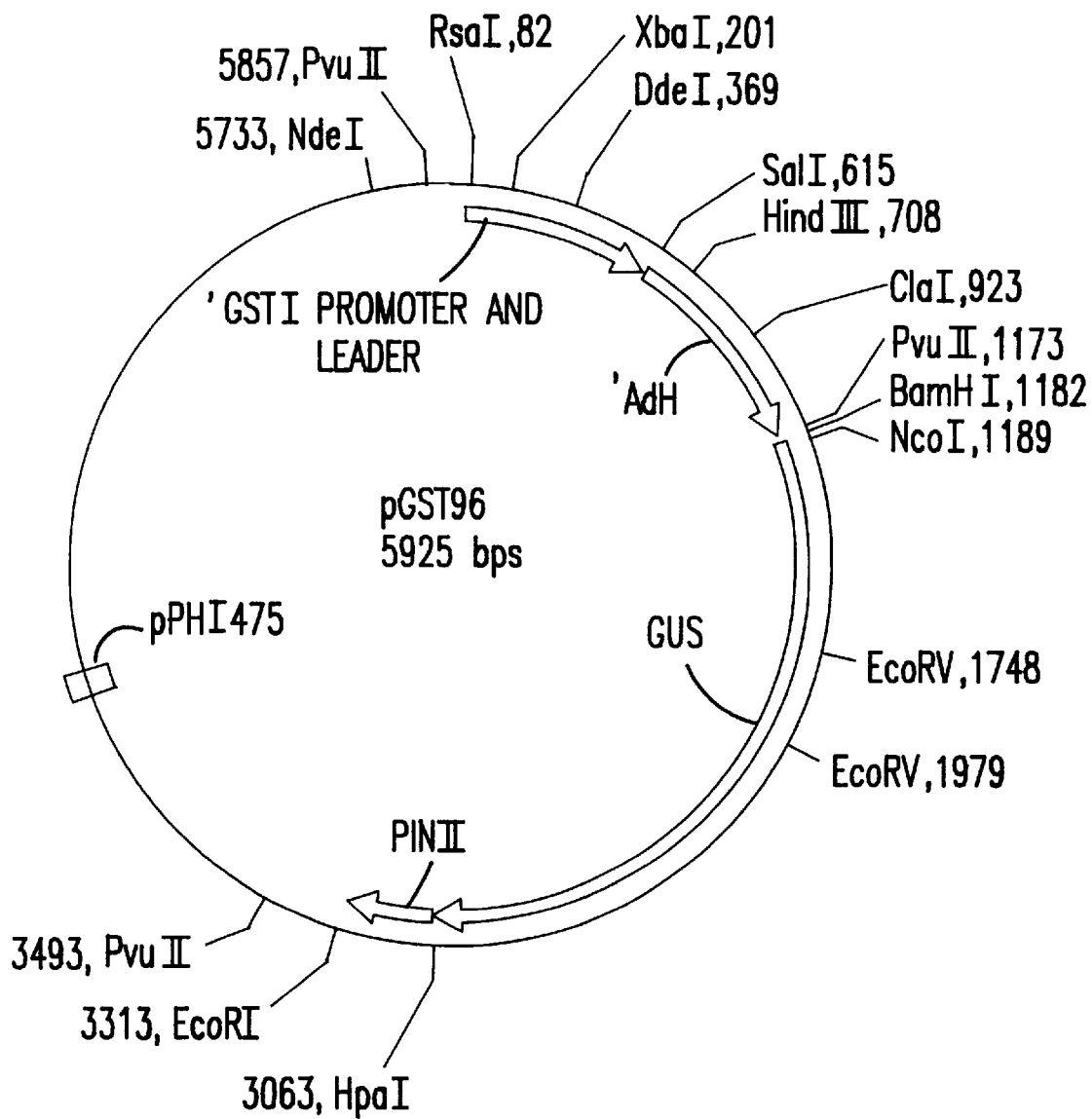
Figure 11:
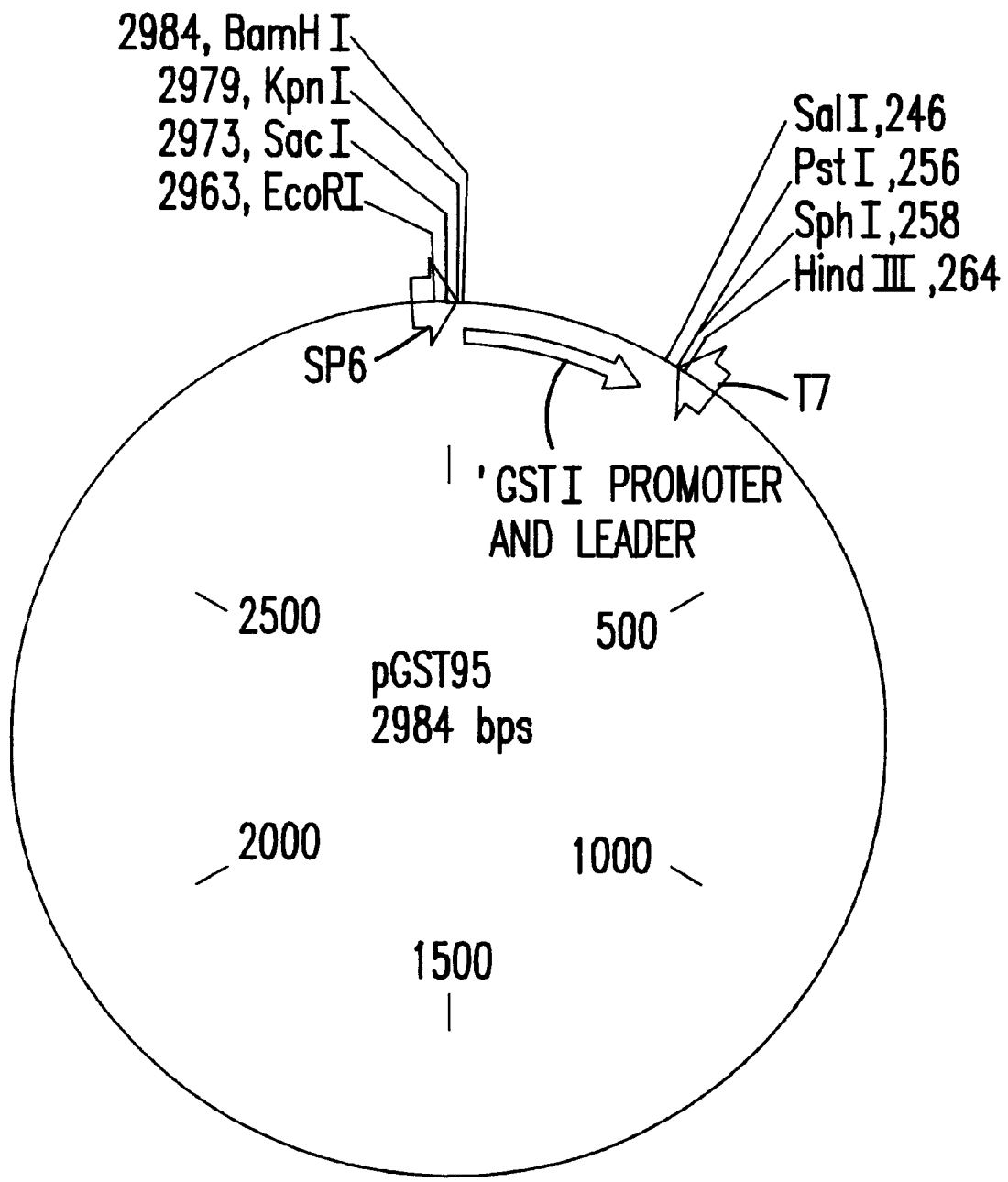
Figure 12:
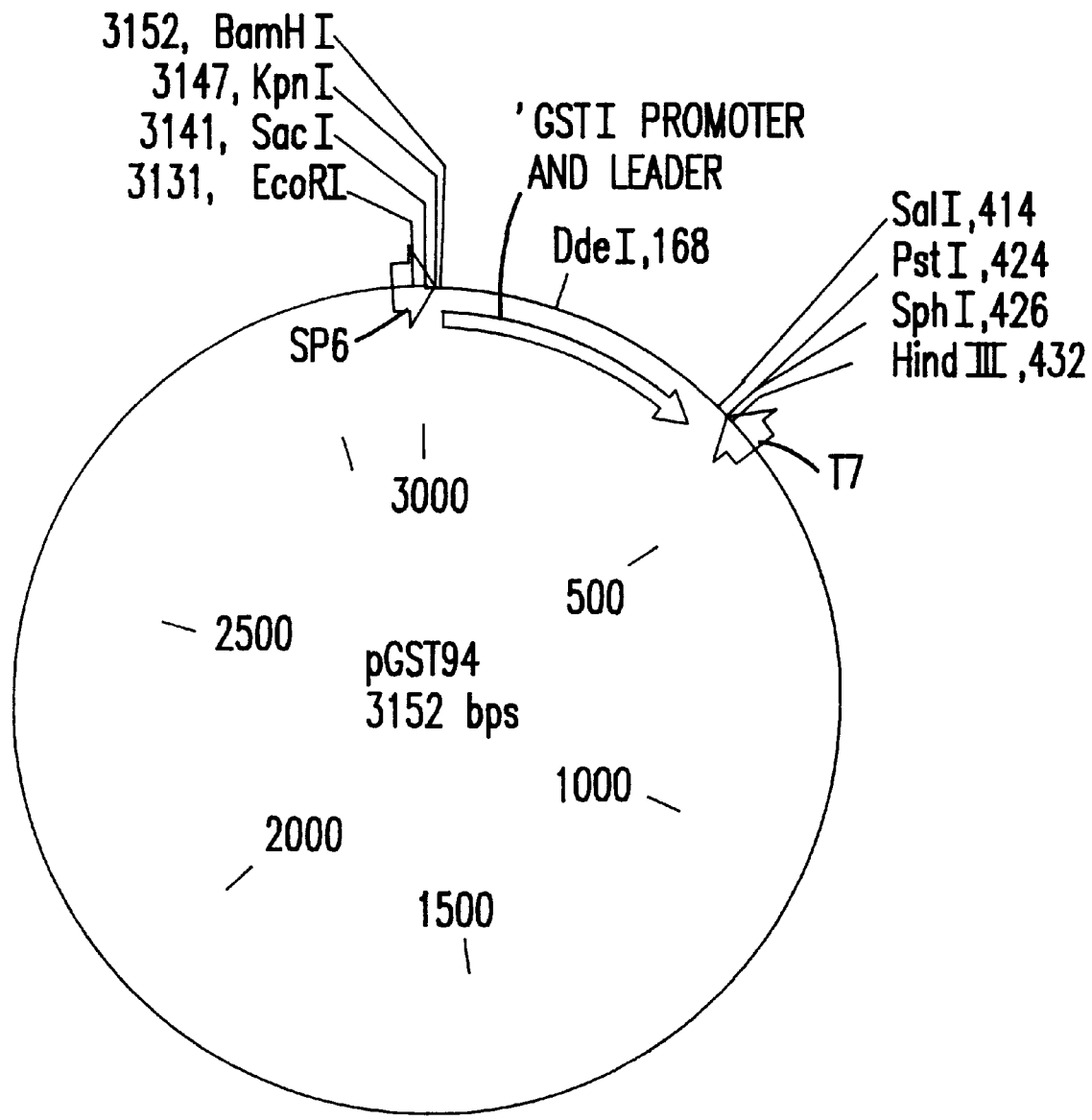
Figure 13:
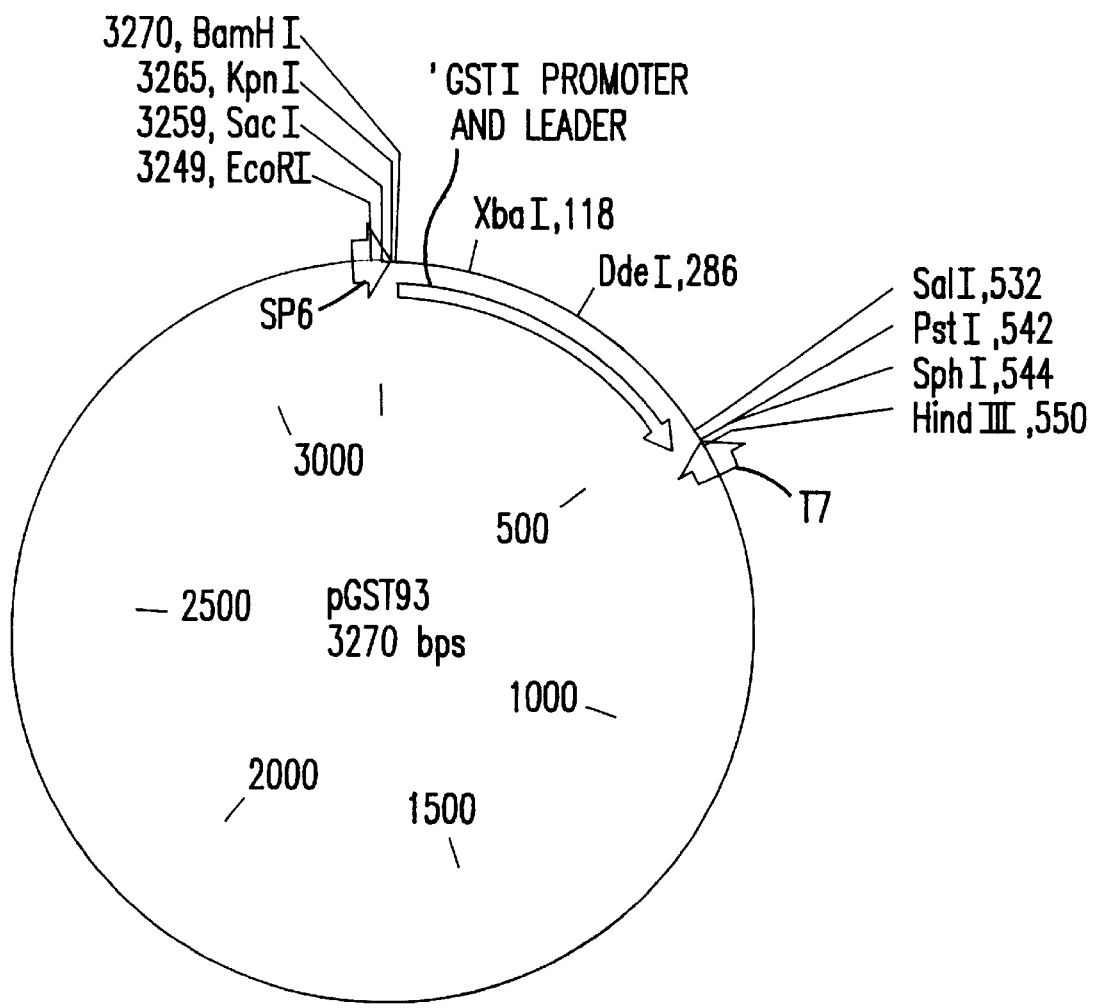
Figure 14:
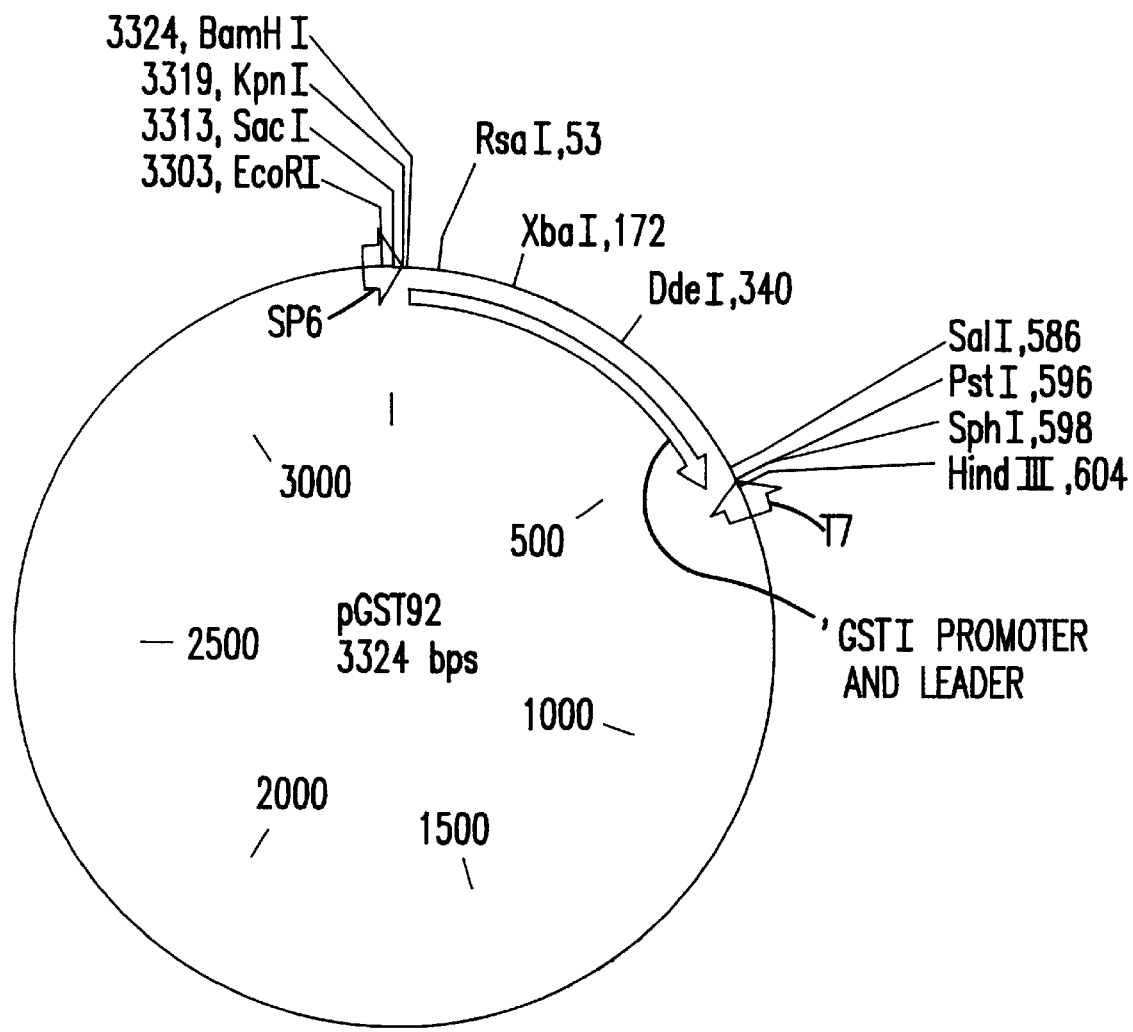

What is claimed is:

1. A plant gene promoter having the sequence listed in SEQ. ID. NO. 1.

2. An expression cassette, comprising a promoter according to claim 1 operatively linked to a gene which codes for a protein other than glutathione-S-transferase, which protein is expressible in a plant.

3. An expression cassette according to claim 2 wherein the protein is a seed storage protein.

4. An expression cassette according to claim 2 wherein the protein is an enzyme other than glutathione-S-transferase.

5. An expression cassette according to claim 2 wherein the protein is a transcriptional activator.

6. An expression cassette according to claim 2 wherein the protein is a lectin.

7. A plant cell, the genome of which comprises an expression cassette according to claim 2.

8. A plant comprising cells according to claim 7.

9. A plant according to claim 8 which is a dicot.

10. A plant according to claim 9 and of a species selected from the group consisting of soybean, rape, sunflower, and alfalfa.

11. A plant according to claim 8 which is a monocot.

12. A plant according to claim 11 and of a species selected from the group consisting of maize, wheat, rice, millet, sorghum, rye, barley, and oat.

* * * * *

```
                          SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
         (A) LENGTH: 861 base pairs
         (B) TYPE: nucelotide
         (C) STRANDEDNESS: double
         (D) TOPOLOGY: linear (ii) MOLECULE TYPE: genomic DNA
         (A) DESCRIPTION:

(iii) HYPOTHETICAL: No (iv) ANTI-SENSE: NO (v) FRAGMENT TYPE:

(vi) ORIGINAL SOURCE:
         (A) ORGANISM: Zea mays
         (B) STRAIN: W22
         (C) INDIVIDUAL ISOLATE:
         (D) DEVELOPMENTAL STAGE:
         (E) HAPLOTYPE:
         (F) TISSUE TYPE:
         (G) CELL TYPE:
         (H) CELL LINE:
         (I) ORGANELLE: Nucleus (vii) IMMEDIATE SOURCE:
         (A) LIBRARY:
         (B) CLONE:

(viii) POSITION IN GENOME:
         (A) CHROMOSOME/SEGMENT: 8L
         (B) MAP POSITION:
         (C) UNITS:

(ix) FEATURE:
         (A) NAME/KEY:
         (B) LOCATION:
         (C) IDENTIFICATION METHOD:
         (D) OTHER INFORMATION:  Includes a PSTI site at 5' end and
```

NCOI site at 3'end.

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO: 1:

```
CTGCAGCCCC CTGCTCATGT GGGCCCCTCG GTGGCGCACT ACCGAGCGTA           50
ATCGCTGGCG TAATCGCGTC TCCTGATCTC TTGCGGTCTT TCCGGACAAT          100
AAAGGGTGT TACTTGGAGG GACTAAAGAT TAGTCTCTAG TTTTTAGTCT           150
TATTTAGTTC TTTTTTTATC AAACACTAGA ACTAAAATAT GAACTAAAAT          200
GATTTAGTCT TTAGTCCTTC ACATATGTGC TAAAATAAAC TAAACCATAT          250
TAATTCCACA TCTACCAGTT CAATTGTACT AATAGCAGAA GAATGTTAAA          300
GACTATTTTA GTCTTATTAT GAGTCATTTA GTATATTTTT TCTATTTTTA          350
GCCTCTACAA ACAAACATGT TAGAGACTAA ATTTTAGTTC TTAGACTAAA          400
GAAACCAAAC ATGACAAAAA CGGACTCGTG TGAAAAGTAA GCAGAAGCAT          450
CTAGACGCGC GGGGGCGGTT GGGGCCTCGC TGACCATCAG AACTGACAAC          500
AGCGCTGCCG CACCTACCCC TCTCCACTAC GACTCCACAT TTTCCAACGG          550
ATTTTTATTT TTCTAAGAAA ATTAGTTTTT TTAGAAAAAT AGAAATCACT          600
TGGTTGCACT AAAAAAGCAG GCACACTCGT CACTCGGTCG CCGCGCGCCC          650
TCCCAGTTCG TCTATTAAAG GGGAACCAGT GAACCACCCG ATGCAACTTG          700
CGTAGAGAGT TGGGCGCAGA GAATAATTTC CCCTTGGTCA CTTGGTGGGC          750
TACGTTGAAC GCATCTCTCA ACCCGCGTCT CTTTCCCCAA GCAAACAAAC          800
AGGGTAGAGG GAGAGGAGAG GAGAGGAGAG GAGAGGAGAG GTTGGGTCTG          850
GGCCACCATG G                                                   861
```